(12) United States Patent
Juola et al.

(10) Patent No.: US 8,965,532 B2
(45) Date of Patent: Feb. 24, 2015

(54) CAPACITIVE MEDICAL ELECTRODE

(76) Inventors: John Juola, Eden Praire, MN (US);
Lloyd Ohme, Minneapolis, MN (US);
Shawn McCutcheon, White Bear Lake, MN (US)

( * ) Notice: Subject to any disclaimer, the term of this patent is extended or adjusted under 35 U.S.C. 154(b) by 344 days.

(21) Appl. No.: 13/042,107

(22) Filed: Mar. 7, 2011

(65) Prior Publication Data

US 2011/0160559 A1 Jun. 30, 2011

Related U.S. Application Data

(63) Continuation of application No. 11/233,980, filed on Sep. 23, 2005, now Pat. No. 7,904,180.

(60) Provisional application No. 60/615,726, filed on Oct. 4, 2004.

(51) Int. Cl.
*A61N 1/00* (2006.01)

(52) U.S. Cl.
USPC .......................................................... 607/142

(58) Field of Classification Search
USPC .......................................................... 607/142
See application file for complete search history.

(56) References Cited

U.S. PATENT DOCUMENTS

| | | |
|---|---|---|
| 3,568,662 A | 3/1971 | Everett |
| 3,744,482 A | 7/1973 | Kaufman |
| 3,882,846 A | 5/1975 | Fletcher |
| 4,166,465 A | 9/1979 | Esty |
| 4,304,235 A | 12/1981 | Kaufman |
| 4,363,162 A | 12/1982 | Price |
| 4,367,755 A | 1/1983 | Bailey |
| 4,387,714 A | 6/1983 | Geddes |
| 4,603,373 A | 7/1986 | Lavene |
| 4,669,468 A | 6/1987 | Cartmell |
| 4,733,328 A | 3/1988 | Blazej |
| 4,763,660 A * | 8/1988 | Kroll et al. ................... 600/391 |
| 4,799,480 A | 1/1989 | Abraham |
| 4,838,273 A | 6/1989 | Cartmell |
| 5,505,200 A | 4/1996 | Takaki |
| 5,746,207 A | 5/1998 | McLaughlin et al. |
| 5,836,942 A | 11/1998 | Netherly |
| 5,849,025 A | 12/1998 | Owens et al. |
| 5,856,029 A | 1/1999 | Burrows |
| 5,947,961 A | 9/1999 | Netherly |

(Continued)

OTHER PUBLICATIONS

Greatbatch, W.B., et al., "Polarization Phenomena Relating to Physiological Electrodes", 1969, Annals of N.Y. Academy of Science 167:722, USA.

(Continued)

*Primary Examiner* — George Manuel
(74) *Attorney, Agent, or Firm* — Moore & Hansen, PLLC (57) ABSTRACT

Medical electrodes in embodiments of the teachings may include one or more of the following features: (a) a metallic conductor, (b) the metallic conductor sandwiched between a first dielectric layer adjacent a top surface of the metallic conductor and a second dielectric layer located on a bottom surface of the metallic conductor, (c) a conducive gel coating on at least one of the first and second dielectric layers, (e) the metallic conductor, the dielectric layers, and the conductive gel being wrapped to form a multi-tiered electrode having a plurality of conductive surfaces, (f) an adhesive adhering the metallic conductor with the dielectric layers, (g) a tab connector to provide a connection to electrical monitoring equipment and (h) an attachment connector to provide electrical connection with a patient.

19 Claims, 12 Drawing Sheets

(56) References Cited

U.S. PATENT DOCUMENTS

| | | |
|---|---|---|
| 6,053,910 A | 4/2000 | Fleenor |
| 6,066,093 A | 5/2000 | Kelly et al. |
| 6,263,226 B1 | 7/2001 | Axelgaard |
| 6,310,760 B1 | 10/2001 | Shaw et al. |
| 6,413,255 B1 | 7/2002 | Stern |
| 6,434,421 B1 | 8/2002 | Taheri |
| 6,544,258 B2 | 4/2003 | Fleenor |
| 2002/0072664 A1 | 6/2002 | Katzenmaier et al. |
| 2003/0036691 A1 | 2/2003 | Stanaland et al. |
| 2004/0015222 A1* | 1/2004 | Nielsen .................. 607/142 |

OTHER PUBLICATIONS

Kim, Yongmin, et al., "Uniformity of Current Density Under Stimulating Electrodes", *Critical Reviews in Biomedical Engineering,* 1990, pp. 585-619, vol. 17, Issue 6, USA.

* cited by examiner

CAPACITIVE MEDICAL ELECTRODE

RELATED APPLICATION

This application is a continuation of U.S. application Ser. No. 11/233,980, filed Sep. 23, 2005 now U.S. Pat. No. 7,904,180, which claims benefit of U.S. Provisional Application No. 60/615,726, filed Oct. 4, 2004, both of which are incorporated herein by reference in their entirety.

TECHNICAL FIELD

The present teachings relate generally to medical electrical sensing and stimulation devices. More particularly the present teachings relate to a capacitance electrode for sensing and reproducing electric potentials at the surface of living tissue and introducing electrical potentials into the tissue.

BACKGROUND

The use of electrodes for sensing electrical activity at the surface of living tissue, such as during the performance of an electroencephalograph (EEG), an electromyograph (EMG), an electrocardiograph (EKG) or a galvanic skin response (GSR) procedure Is well known. These electrodes and others are also used for stimulating living tissue, e.g., TENS (Transcutaneous Electric Nerve Stimulation), defibrillation, pacing (internal and external), or for transferring energy from electrical devices to the body as in electrocautery. These and other prior electrodes provide resistive coupling to the test subject, so as to facilitate the monitoring of electrical activity therein or contain a metallic conductor in chemical contact with an electrolytic medium.

Resistively coupled electrodes have proved to be generally suitable for their intended purposes, however, these electrodes do possess inherent deficiencies, which detract from their utility. For example, resistively coupled electrodes can consume a lot of power, which is undesirable for battery driven devices. Further, they can generate a substantial amount of heat, which can cause burns in defibrillation applications.

Additionally, there are limitations that may occur with both the sensing and stimulation applications using resistively coupled electrodes. Motion artifact, half-cell potential, and non-linearity or distortions of the signal at the electrode-electrolyte interface are some of the limitations that may occur with sensing applications. In stimulation applications, limitations also include non-uniform current density, spikes in amplitude at the onset of the signal, and resistive power loss. All of which are related to the electrode-patient interface.

The transmission of an electrical signal between an electrode and an ionic medium involves certain capacitive and chemical issues. Current exists in metal as a flow of electrons through the crystal lattice of the material. In contrast, current in an ionic solution requires the movement of cations and/or anions through the solution. The electrical interaction between metal and an ionic solution can occur as a capacitive process, an inductive process, or as a chemical reaction.

Typically, both capacitive and chemical interactions take place during electrical activity between a patient and an electrode. The volume of ionic solution on a metal is called the Helmholtz double layer and contains both the capacitive and chemical reactions. Generally all electrodes have a capacitive component except for silver/silver chloride electrodes, commonly used for ECG sensing, at small currents. Additionally, platinum or other inert metals can transmit signals in a purely capacitive mode, but also at small currents only.

The nature of the reaction for most electrodes depends on multiple factors. Generally, the metal composition of the electrode determines the threshold at which chemical reaction will occur, and what they will be, presuming a saline ionic solution. Most metals, including stainless steel, will produce hydrogen and chlorine gases as a byproduct of the chemical reaction of the metal with the ionic solution. This is undesirable because chlorine gas can possibly irritate the patient's tissue at the anode. Further, these gases can cause corrosion of the electrode itself.

Generally, all electrodes, except for silver/silver chloride electrodes and a few others, have a strong capacitive component. Silver/silver chloride avoids this capacitive component at small currents by anodal chloridization of the electrode surface. However, the silver/silver chloride electrodes create a capacitive interference with large currents. Electrochemical polarization of physiological electrodes is an undesirable but seemingly unavoidable phenomenon that detracts from the performance of implanted electronic prosthetic devices. In the case of noble metals, polarization causes a significant waste of stimulation energy at the electrode surface. With non-noble metals, the energy waste is even greater and may involve electrolytic corrosion reactions. Such corrosion may destroy the electrode and may possibly leave toxic residues in body tissues. The electrode-electrolyte interface presents to a cardiac pacemaker a highly capacitive load having multiple time constants of the same order of magnitude as the I- or 2-millisecond (msec) duration of a pacemaking impulse. Thus, an applied square wave of current on the electrodes does not obey Ohm's law and does not elicit a square wave of voltage, nor is the voltage waveform a constant slope (ramp), as would be expected from a single lumped capacitor. Rather, the voltage rises in less than a microsecond to an initial value and then more slowly, in at least two different time constants, until the end of the pulse. This capacitive interference complicates stimulation with this type of electrode.

It has been found that platinum electrodes can avoid toxicity since they produce only a small amount of chlorine. However, approximately 60% of the current through a platinum pacemaker electrode occurs through capacitance. Thus existing simulation electrodes mostly include capacitive effects, however, the capacitance is complex and extremely variable. This capacitance is undesirable for several reasons. The capacitance varies in a nonlinear fashion with a myriad of parameters including temperature and rate of change of the electrical signal coming from the patient. This capacitance degrades the electrical signal coming from the patient and is impossible to model for filtering purposes. Further, the capacitance's resistive component also degrades the electrical signal. There are at least two ways the chemical reactions occurring at the electrode surface affect electrical signals. First, is the formation of gas bubbles, which act as a physical barrier to current passage. Second, the half-cell potential changes with small perturbations in the physical environment, creating electrical noise.

Purely capacitive electrodes solve this problem since they avoid chemical reactions all together, but existing technology limits their applications. An example of a purely capacitive electrode is dispersive electrodes used in electrocautery. These electrodes consist of a sheet of metal and a non-conductive adhesive gel in contact with the skin. The adhesive gel has low conductivity but a high dielectric constant. The metal foil forms one plate of the capacitor and the skin forms the other. The capacitance of these electrodes typically ranges in the Pico farad range. Because the electrocautery unit operates in the 400-kilohertz range, the reactance is low.

Dispersive electrodes also require a low impedance interface. Resistive dispersive electrodes can monitor the adequacy of the contact between the electrode and the patient's body by contact quality monitoring ("CQM") circuitry in an electrosurgical generator. Current generator systems have safety circuits, which can detect when a resistive electrode does not have good attachment to the body. If something has caused the electrode to be applied without adequate initial contact with the body or some event during surgery has caused the adequate initial contact to become inadequate, these safety circuits will detect that problem and terminate the current being applied.

While existing capacitive electrodes do not have the edge effect (electrical fields on the edge of the electrode) of concern for resistive type dispersive electrodes and the current transfer is much more uniform across the surface of the electrode compared to resistive types, they are not compatible with the above described CQM circuits, and thus when used do not have this protection against inadvertent misapplication of electrocautery units used during electrosurgery. Lossy dielectric designs, such as the design described in U.S. Pat. No. 5,836,942, overcome this problem, but the design's resistive component adds to unwanted heat generation. Problems faced by designers of medical electrodes include minimizing overall heat generation and maximizing uniformity of the current density.

Another disadvantage associated with traditional stimulating electrodes, is they often cause an initial uncomfortable shock before attaining a stable sensation.

In view of the foregoing, it is desirable to provide an electrode suitable for use in EEG, EMG, EKG, and GSR procedures and the like overcoming the disadvantages of the prior art by manipulating the electrode-electrolyte interface of a medical electrode in contact with a biological system and providing a large capacitance in a standard sized electrode. It is desirable to have a substantially capacitive electrode to avoid chemical reactions. Additionally it is desirable to have an electrode with a constant predictable capacitance and that can avoid a half-cell potential.

SUMMARY

A method of manufacturing a medical electrode in embodiments of the teachings may include one or more of the following features: (a) coating layers of dielectric film having a metallic conductor sandwiched between said layers with a conductive gel, (b) wrapping the metallic conductor sandwiched between the layers of dielectric to form a multi-tiered electrode having a plurality of conductive surfaces, (c) placing the multi-tiered electrode into a plastic case, (d) gluing the metallic conductor to the dielectric layers, (e) wherein the dielectric layers is a capacitive grade Mylar, (f) wherein the metallic conductor is conductive ink, (g) wherein the metallic conductor is silver, (h) wherein the plurality of conductive surfaces can be capacitively coupled to a patient, (i) wherein there is no chemical reaction between the metallic conductor and the conductive gel, and (j) wherein there is no galvanic contact between the metallic conductor and the conductive gel.

A medical electrode according to the present teachings may include one or more of the following features: (a) a metallic conductor, (b) a first dielectric layer adjacent a top surface of the metallic conductor, (c) a second dielectric layer located on a bottom surface of the metallic conductor, (d) a conductive gel coating on at least one of the first and second dielectric layers, (e) wherein the metallic conductor has a plurality of conductive sections, (f) wherein the conductive sections are in capacitive communication with adjacent sections, (g) wherein the dielectric layers are a capacitive grade Mylar, (h) wherein the metallic conductor is conductive ink, (i) wherein the metallic conductor is silver, (j) wherein the plurality of conductive sections can be capacitively coupled to a patient, (k) wherein there is no chemical reaction between the metallic conductor and the conductive gel, and (l) wherein there is no galvanic contact between the metallic conductor and the conductive gel.

A medical electrode according to the present teachings may include one or more of the following features: (a) a metallic conductor, the metallic conductor sandwiched between a first dielectric layer adjacent a top surface of the metallic conductor and a second dielectric layer located on a bottom surface of the metallic conductor, (b) a conductive gel coating on at least one of the first and second dielectric layers, the metallic conductor, the dielectric layers, and the conductive gel being wrapped to form a multi-tiered electrode having a plurality of conductive surfaces, (c) an adhesive adhering the metallic conductor with the dielectric layers, (d) a tab connector to provide a connection to electrical monitoring equipment, (e) an attachment connector to provide electrical connection with a patient, (f) wherein the metallic conductor is electrochemically isolated from the patient so that there is no galvanic interaction between them, and (g) wherein the dielectric layers allow the transfer of electrical signals and energy to and from the metallic conductor and the patient.

A medical electrode according to the present teachings may include one or more of the following features: (a) a plurality of metallic conductors, the metallic conductors sandwiched between a first dielectric layer adjacent a top surface of the metallic conductors and a second dielectric layer located on a bottom surface of the metallic conductors; and (b) a conductive gel coating on at least one of the first and second dielectric layers, the metallic conductors, the dielectric layers, and the conductive gel being layered to form a multi-tiered electrode having a plurality of conductive surfaces.

A medical electrode according to the present teaching may include one or more of the following features: (a) a plastic rim, (b) a plurality of wire stands wrapped around the plastic rim, the wire strands spaced apart to form a plurality of conductive surfaces, and a high dielectric material isolating the rim and wire strands from a patient.

DETAILED DESCRIPTION

The following discussion is presented to enable a person skilled in the art to make and use the present teachings. Various modifications to the illustrated embodiments will be readily apparent to those skilled in the art, and the generic principles herein may be applied to other embodiments and applications without departing from the present teachings. Thus, the present teachings are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the present teachings. Skilled artisans will recognize the examples provided herein have many useful alternatives and fall within the scope of the present teachings.

Figure 1:
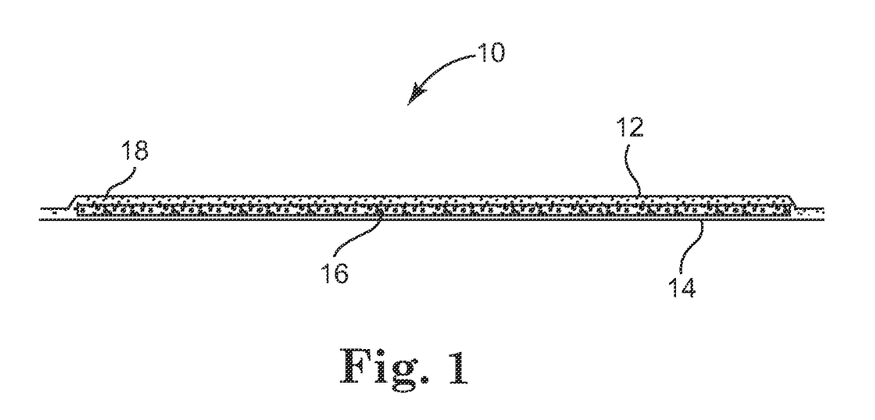
FIG. 1 is a side profile view of a medical electrode in an embodiment according to the present teachings.

With reference to FIG. 1, a side profile view of a medical electrode in an embodiment according to the present teachings is shown. Electrode 10 can include an upper dielectric layer 12 and a lower dielectric layer 14 and a conductive metal 16 sandwiched between layers 12 and 14. Layers 12 and 14 can be held together with a thin layer of adhesive 18. Dielectric layers 12 and 14 can be made of a capacitive grade Mylar, however it is contemplated that layers 12 and 14 could be made of most any dielectric material such as cellophane, cellulose, acetate resin, Neoprene, or polyvinylchloride, for example without departing from the spirit of the teachings. Further, conductive metal 16 can be comprised of silver ink, however, conductive metal 16 can be comprised of most any conductive material such as carbon, gold, platinum, copper, or stainless steel, for example without departing from the spirit of the teachings. As illustrated adhesive 18 can be a pressure sensitive biocompatible glue, however, most any type of adhesive could be used such as polyurethane, hot melt, or aqueous adhesive emulsion, for example without departing from the spirit of the teachings. As illustrated, electrode 10 can be comprised of layers 12 and 14 having a thickness of about 0.5 mil, conductor 16 with a thickness of about 0.30 Mil, and adhesive layer 18 with a thickness or about 0.43 mil.

Figure 2:
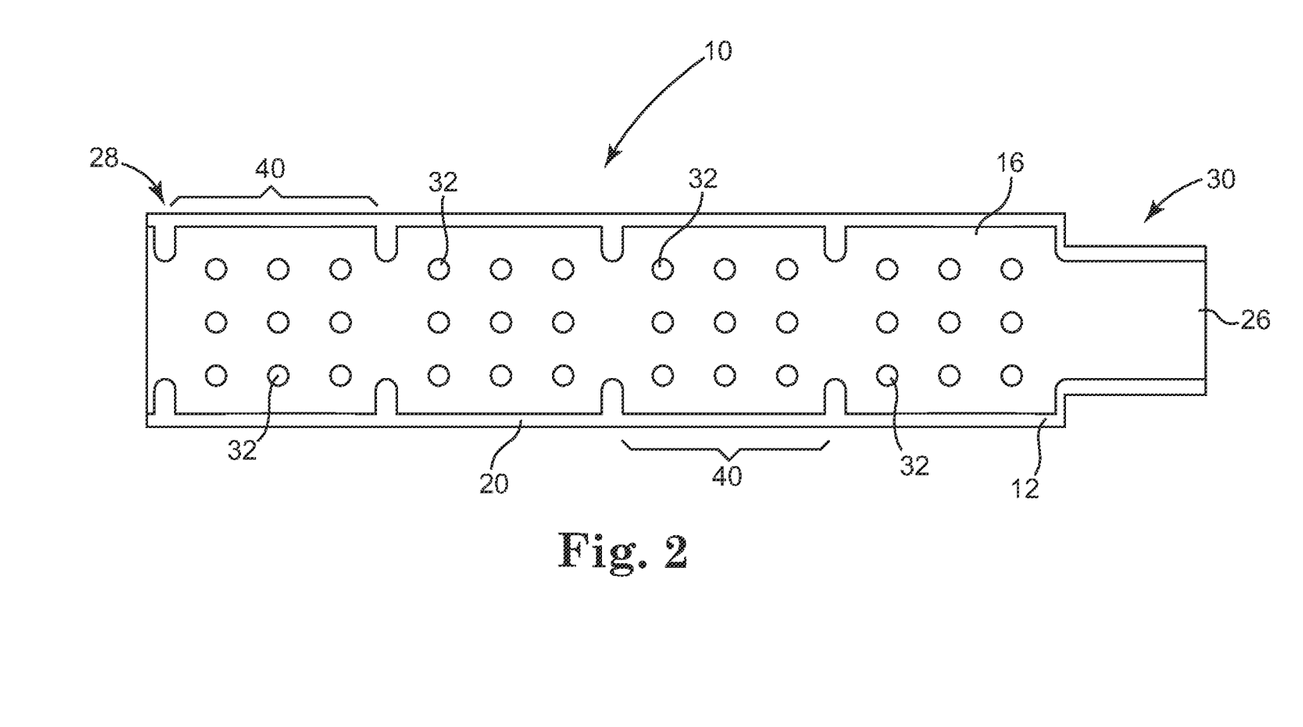
FIG. 2 is a top profile view of the medical electrode shown in FIG. 1 in an embodiment according to the present teachings.
Figure 2A:
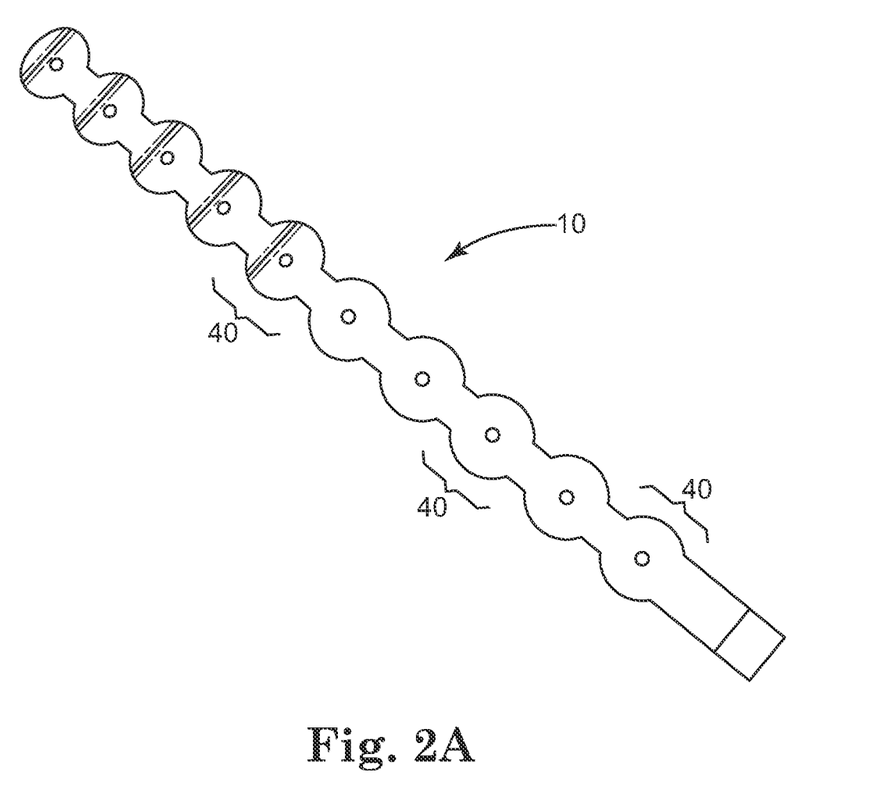
FIG. 2A is a top profile view of a medical electrode in an embodiment according to the present teachings.
Figure 2B:
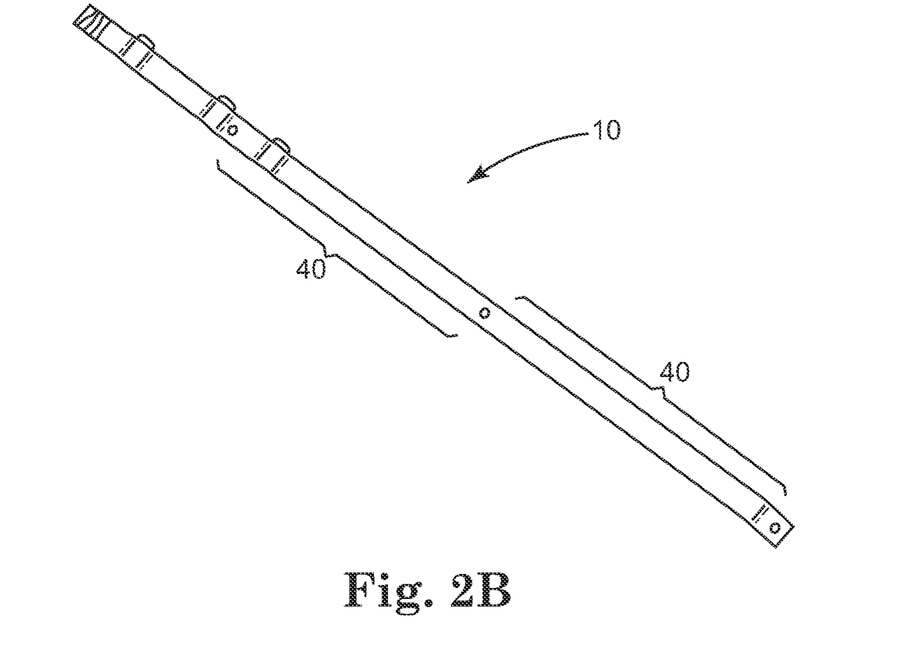
FIG. 2B is a top profile view of a medical electrode in an embodiment according to the present teachings.
Figure 3:
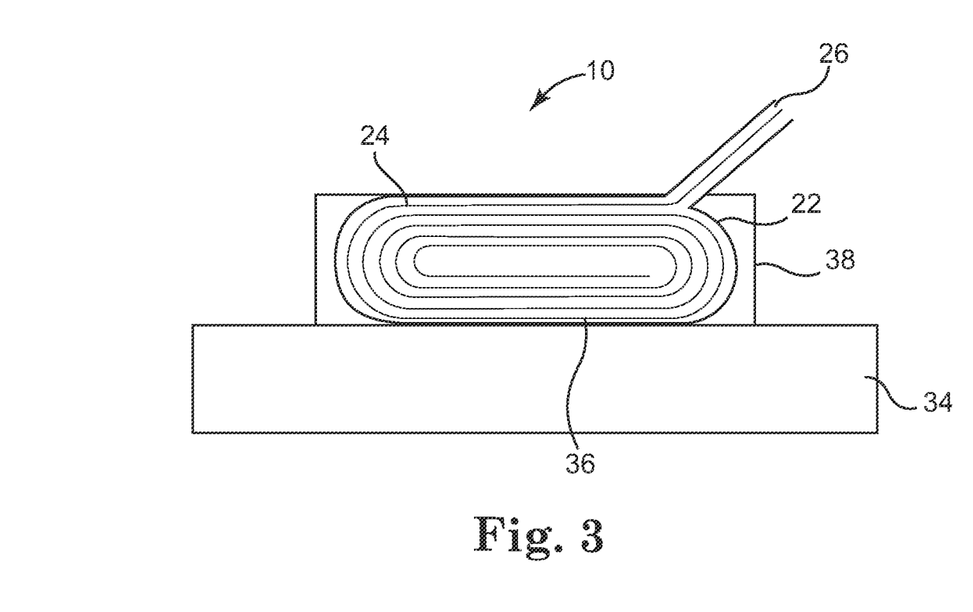
FIG. 3 is a side profile view of a multi-tiered medical electrode in an embodiment according to the present teachings.

With reference to FIG. 2, a top profile view of the medical electrode shown in FIG. 1 in an embodiment according to the present teachings is shown. When layers 12 and 14 are adhered together with adhesive 18 sandwiching conductor 16, electrode 10 appears in the form of strip 20. Strip 20 may then be coated with a conductive gel 22 (FIG. 3). Coating gel 22 can be comprised of a conducting hydrogel, however, conductive gel 22 can be most any type of conductive substance, such as standard medical electrode gels, for example without departing from the spirit of the teachings. Gel 22 can be applied to both layer 12 and 14. Strip 20 can be lengthened to achieve a higher capacitance, shortened to achieve a lower capacitance, and manufactured to a specific length to achieve a desired capacitance. Sections 40 are chosen for their size in that they have approximately the same surface area as a standard medical electrode. Further, sections 40 are chosen by the size of capacitance they will have. For example, each section 40 can be 1.5 inches in length and can have a capacitance of 7 nanofarads. Therefore a strip of ten sections 40 would achieve a total capacitance of approximately 70 nanofarads, which has been found to perform well. By knowing the capacitance of each section 40 of strip 20, it is relatively easy to custom manufacture electrodes based upon the need of the user. Further, it is not necessary for section 40 to have a square shape. As shown in FIG. 2A, electrode 10 can have sections 40 with a circular shape. FIG. 2B shows an electrode 10 having sections 40 with a rectangular shape. The shapes can be chosen depending on the application electrode 10 will be used for and/or which shape provides the desired capacitance. Conductive metal 16 can be solid with holes 32, however, conductive metal can also be a mesh, wire frame, or segmented without departing from the spirit of the invention.

With reference to FIG. 3, a side profile view of a multi-tiered medical electrode in an embodiment according to the present teachings is shown. After conductive gel 22 is applied, strip 20 can be rolled or folded section 40 over section 40 from distal end 28 to proximal end 30 into a three-dimensional structure 24 to insure all surfaces of strip 20 are in electrical communication with a biological system 34, such as a patient as will be described in more detail below. After strip 20 is rolled into multi-tiered structure 24, mull-tiered structure 24 can be placed into plastic case 38, which holds electrode 10 into a lightly wound or folded multi-tiered structure 24. A tab connector 26 can be provided at proximal end 30 to provide a connection to electrical monitoring equipment (not shown), such as an EEG, an EMG, or an ECG, for example. Adhesive 18 and gel 22 are not applied to tab 26 so an external connector (not shown) can be applied to conductor 16. Holes 32 can be located in electrode 10 to facilitate conduction of an electrical signal to and from skin or tissue 34. Holes 32 allow for conduction of an electrical signal from the upper layers of structure 24 through gel 22 to the patient. Each hole 32 can extend completely through strip 20. There is approximately a 2 mm strip around hole 32 where the is no silver ink coated on strip 20. Holes 32 allow the current to travel down through structure 24. Without holes 32 all of the current would travel along the outer edge of electrode 10 except for the portion of strip 20 closest to the patient's skin. Thus holes 32 shorten the current path to the patient considerably and thus decrease the resistance of electrode 10. It's also of note that conducting gel 22 overlaps the outer edge of electrode 10 providing another path to the patient. As illustrated, holes 32 are placed at regular intervals. By having holes 32 at regular intervals the conductive path from the upper layers to the skin can be shortened. However, it is fully contemplated holes 32 can be at irregular intervals and randomly placed without departing from the spirit of the present teachings.

The present teachings overcome the disadvantages associated with some prior art systems by manipulating the electrode-electrolyte interface of medical electrode 10 in contact with biological system 34. As discussed above, one embodiment of the present teachings provides conductor 16, which can be isolated from gel 22 so there is no galvanic contact between gel 22 and conductor 16, though not excluding galvanic contact with other components of the system, such as layer 14. The dielectric properties of layers 12 and 14 not only prevent any galvanic contact between gel 22 and conductor 16, but also allows for the transfer of electrical signals and energy to and from conductor 16. Further, layers 12 and 14 eliminate any chemical interactions between gel 22 and electrode 10. The folded or rolled structure 24 also maximizes the surface area of electrode 10 through its multi-tiered structure 24. The function of structure 24 is to allow a large capacitance in a standard sized electrode through multi-tiered conductor 24, which provides a large capacitance when connected to an A/C power source.

As stated above, the variables of note in an electrode design are the uniformity of the current density, the impedance, and (for internal electrodes) the toxicity. Purely capacitive electrode 10 provides a more biocompatible surface and also eliminates any oxidation-reduction reactions at interface 36. Oxidation or reduction reactions at the electrode-electrolyte interface 36 set up an electrical potential, which can be measured, called a half-cell potential. Half-cell potential is sensitive to physical perturbations in the environment. The fluctuations in half-cell potential constitute an alternating current that is transmitted through patient electrode interface 36 creating a noisy signal. By eliminating half-cell potential, one source of motion artifact can be eliminated. It is of note that even in platinum electrodes monitoring small signals, the half-cell potential produces noise, even though the system is perfectly polarized. Since layers 12 and 14 are sandwiched between conductor 16 and gel 22, there is no chemical reaction to affect the capacitance of electrode 10. Therefore, since the capacitance is fixed in electrode 10 and does not vary with surface and signal characteristics, there are minimal motion artifact results. Further, electrode 10 and skin 34 are in series with the resistance of whatever monitor is connected to electrode 10. This constitutes an RC circuit, which can be tuned to a particular frequency band. Thus, the electrical signals of a patient can be more efficiently monitored without distortion or loss.

Figure 4:
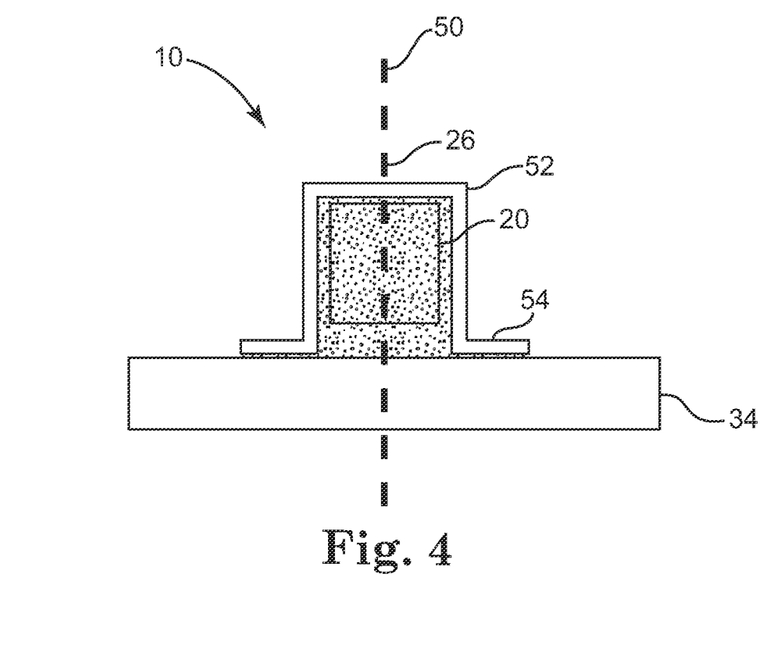
FIG. 4 is a side profile view of a multi-tiered medical electrode in an embodiment according to the present teachings.
Figure 4A:
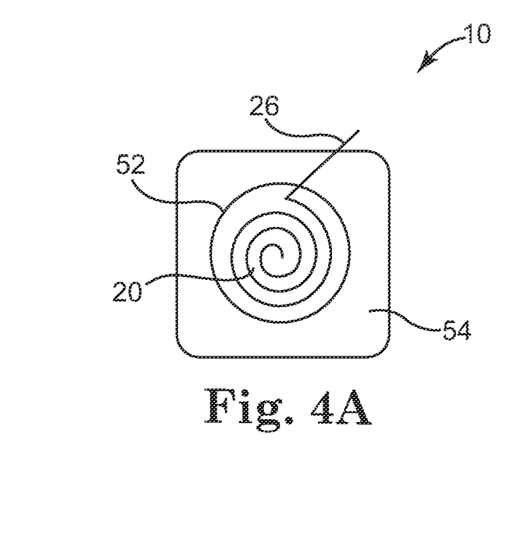
FIG. 4A is an overhead profile view of a multi-tiered medical electrode in an embodiment according to the present teachings.

With reference to FIGS. 4 & 4A, a side and top profile view of a multi-tiered medical electrode in an embodiment according to the present teachings is shown respectively. Electrode 10 can be oriented so that a central axis 50 of electrode 10 is perpendicular to skin 34 in a "jellyroll" configuration. This orientation provides a more uniform current density since all layers contribute equally. As can be seen from FIG. 4A, strip 20 is rolled in contrast to strip 20 shown in FIG. 3, which is folded. After strip 20 is rolled it can be placed in a case 52 and then attached to a base plate 54, which is made of an insulation material. Base plate 54 is utilized to stabilize electrode 10 as it sits upon the patient's skin 34. Without base plate 54, electrode 10 would have trouble remaining upright and would easily fall over and roll off of the patient.

Figure 5:
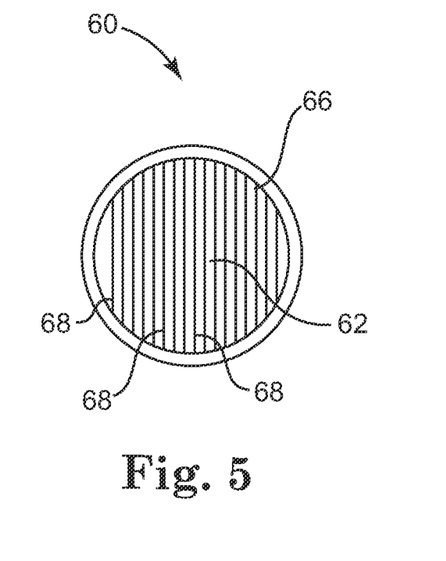
FIG. 5 is a overhead profile view of a TENS medical electrode in an embodiment according to the present teachings.
Figure 5A:
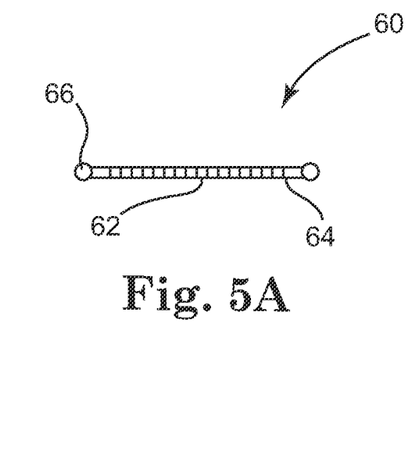
FIG. 5A is an side profile view of a TENS medical electrode in an embodiment according to the present teachings.
Figure 7:
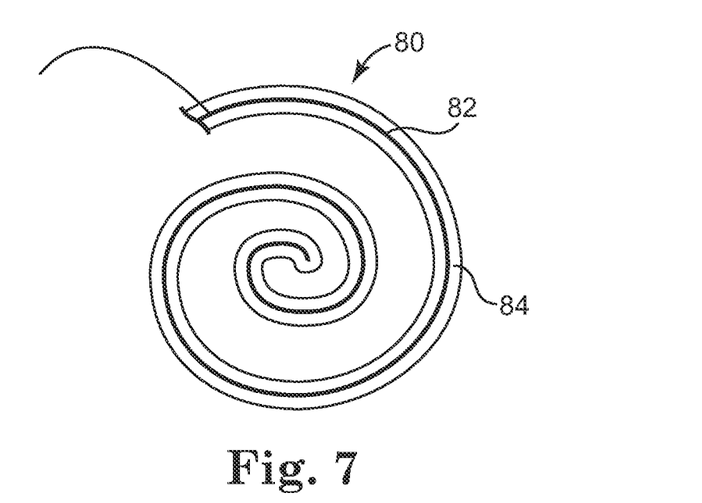
FIG. 7 is an overhead profile view of an implanted pacing/defibrillation medical electrode in an embodiment according to the present teachings.

With reference to FIGS. 5 & 5A, a top and side profile view of a TENS medical electrode in an embodiment according to the present teachings is shown respectively. A TENS electrode 60 consists of wire mesh 62 wrapped around plastic rim 66 and insulated with a high dielectric material 64 which is biocompatible and inert such as Formvar enamel. This wire mesh design provides for a robust electrode lending itself to use as an implantable electrode, which would be in direct contact with body fluids instead of a conducting gel. As illustrated, dielectric material 64 is made of Formvar enamel, however it is contemplated material 64 could be made of most any dielectric material such as glass or polyvinylchloride, for example without departing from the spirit of the teachings. In this application, wire mesh 62 provides the purely capacitive multi-tiered component. The purely capacitive component is created by the multiple capacitances in-between each strand 68 of wire mesh 62. Wire mesh 62 can be made of copper, however, wire mesh 62 can be made of most any conductive metal such as gold, platinum, silver, or stainless steel, for example, without departing from the spirit of the teachings. Similar to multi-tiered structure 24 discussed above, electrode 60 is tiered horizontally to a patient's skin to provide the capacitive component similar to the electrode structure of FIGS. 4 and 4A. The distance between wire lengths determines the electrical communication with an electrolytic medium and determines the capacitive value of electrode 60. It's helpful if strands 68 don't come in contact with each other thus possibly decreasing the effective surface area. A randomly wound structure could be utilized, however, the inventors have discovered this structure performed inferiorly when compared to the structure shown in FIG. 5 due to the wire insulation possibly cracking when randomly compressed. The structure of the electrode varies with the application. While the basic design is a wire mesh, the shape of the rim and the number of layers can be varied, for example, without departing from the spirit of the invention. As illustrated in FIG. 7, one variation without a rim provides flexibility for insertion. Other variations include a braided structure, such as a "rope" electrode.

In contrast to prior electrodes, the present teaching discloses electrode 60 has even lower impedance than previous capacitive electrodes. In the present teachings, the relatively high capacitance minimizes or lowers the significance of the reactance. Present TENS electrodes sometimes use high resistance materials such as carbonized rubber in order to achieve uniform current density. This resistance is undesirable as discussed above. A capacitive electrode with low Impedance would provide a uniform current density unlike a resistive electrode. The lower impedance, which occurs as reactance, results in lower power consumption than resistive electrodes discussed above. This proves to be especially useful when electrode 60 is being used in applications utilizing batteries by greatly prolonging battery life.

Figure 6:
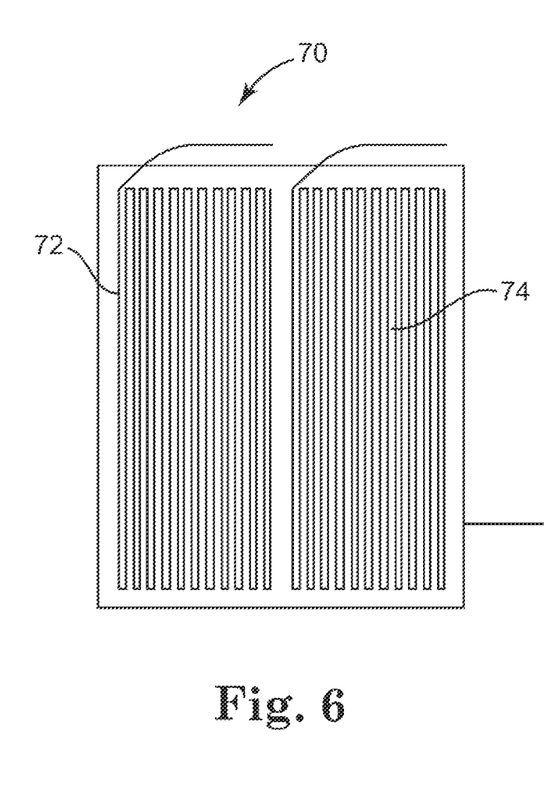
FIG. 6 is an overhead profile view of a dispersive medical electrode in an embodiment according to the present teachings.
Figure 6A:
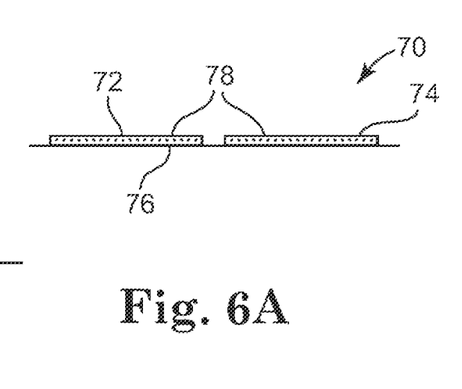
FIG. 6A is a side profile view of a dispersive medical electrode in an embodiment according to the present teachings.

FIGS. 6 and 6A is a side and top profile view of a dispersive medical electrode in embodiments according to the present teachings is shown respectively. The structure of dispersive electrode 70 minimizes overall heat generation and maximizes uniformity of the current density. Electrode 70 provides very low impedance, a large part of which is reactance. Electrode 70 can have a first grid 72 and a second grid 74 which are isolated from each other. Grids 72 & 74 rest upon and are attached to insulated backing 76 comprised of Latex material, however, most any type of insulative material could be utilized without departing from the spirit of the teachings. A gel 78, such as discussed above is then applied to the grids 72 and 74. Grids 72 & 74 are comprised of copper, however, grids 72 & 74 can be comprised of most any conductive metal such as gold, platinum, silver, or stainless steel, for example, without departing from the spirit of the teachings. While electrode 70 capacitive electrode, it allows for use of the safety mechanisms of electrocautery units, such as the contact quality monitoring (CQM) system. This system monitors contact with a patient's skin by comparing the impedance between grids 72 & 74. If the electrode contact is compromised, the CQM disables the electrocautery, thus preventing burns. One could also employ Mylar strip electrodes in a similar manner.

With reference to FIG. 7, an overhead profile view of an implanted pacing/defibrillation medical electrode in an embodiment according to the present teachings is shown. Pacing/defibrillation electrode 80 consists of a length of steel wire 82, formed in a spiral. Electrode 80 can be formed of steel wire 82; however, electrode 80 can be formed of most any conductive metal such as gold, platinum, copper, or stainless steel, for example, without departing from the spirit of the teachings. Electrode 80 would, similar to the other electrodes discussed above, be coated with a material, which has a good biocompatibility and a high dielectric constant. The biocompatibility would allow for insertion into a patient and the dielectric would allow for electrical contact between the patient and wire 82 while preventing any chemical reaction between wire 82 and the patient. Electrode 80 could be straightened and threaded into a hollow catheter for insertion. Once the tip of the catheter was attached to the endocardium, the catheter would be removed and the electrode would assume a predetermined shape such as a spiral.

Pacing/defibrillation electrode 80 provides another embodiment where the technology of the present teachings would improve existing electrodes. Present pacing/defibrillation leads sacrifice uniformity of current density for low impedance. Capacitive leads have an inherently better current uniformity as discussed above.

Figure 8:
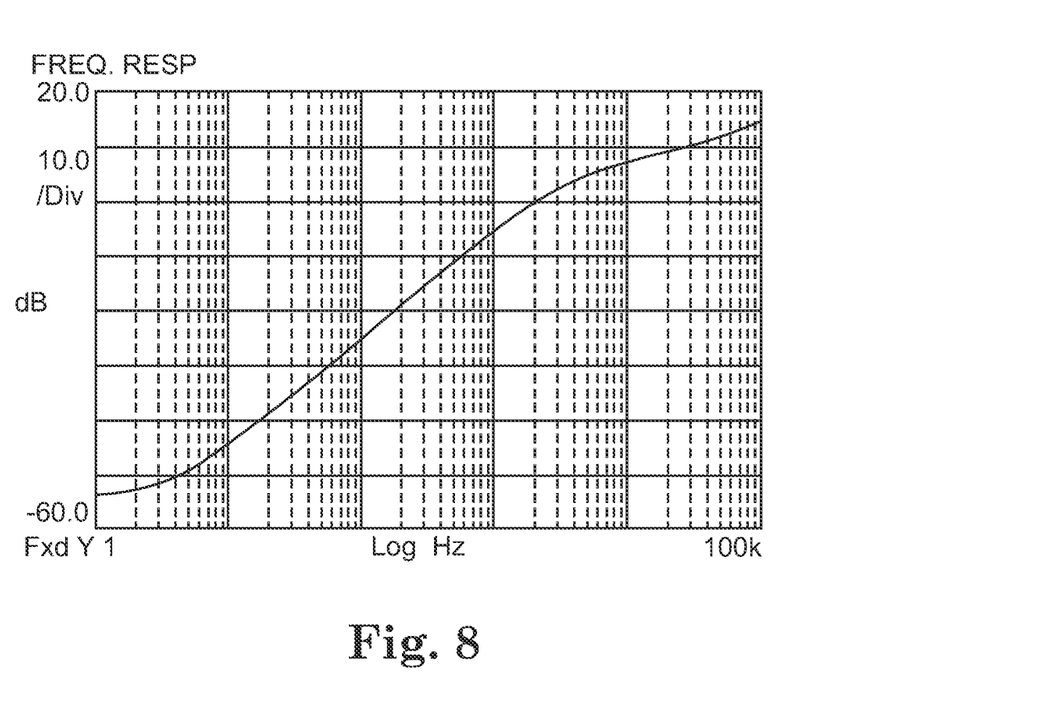
FIG. 8 is a frequency response curve representation taken from a medical electrode in an embodiment according to the present teachings.

With reference to FIG. 8, a frequency response curve representation taken from a medical electrode in an embodiment according to the present teachings is shown. One skilled in the art can readily see the electrodes of the present teachings function as an RC circuit when applied to the patient and connected to a monitor. FIG. 8, shows conductivity versus frequency for a wire electrode. As can be seen there is no shift in phase angle over the selected range of an electrode pair according to the prevent teachings. There is a frequency range where there is little loss of signal, but a drop off at both the high and low ends. The plot of FIG. 8 shows that the capacitance of the electrode of the present teachings is predictable.

Figure 9:
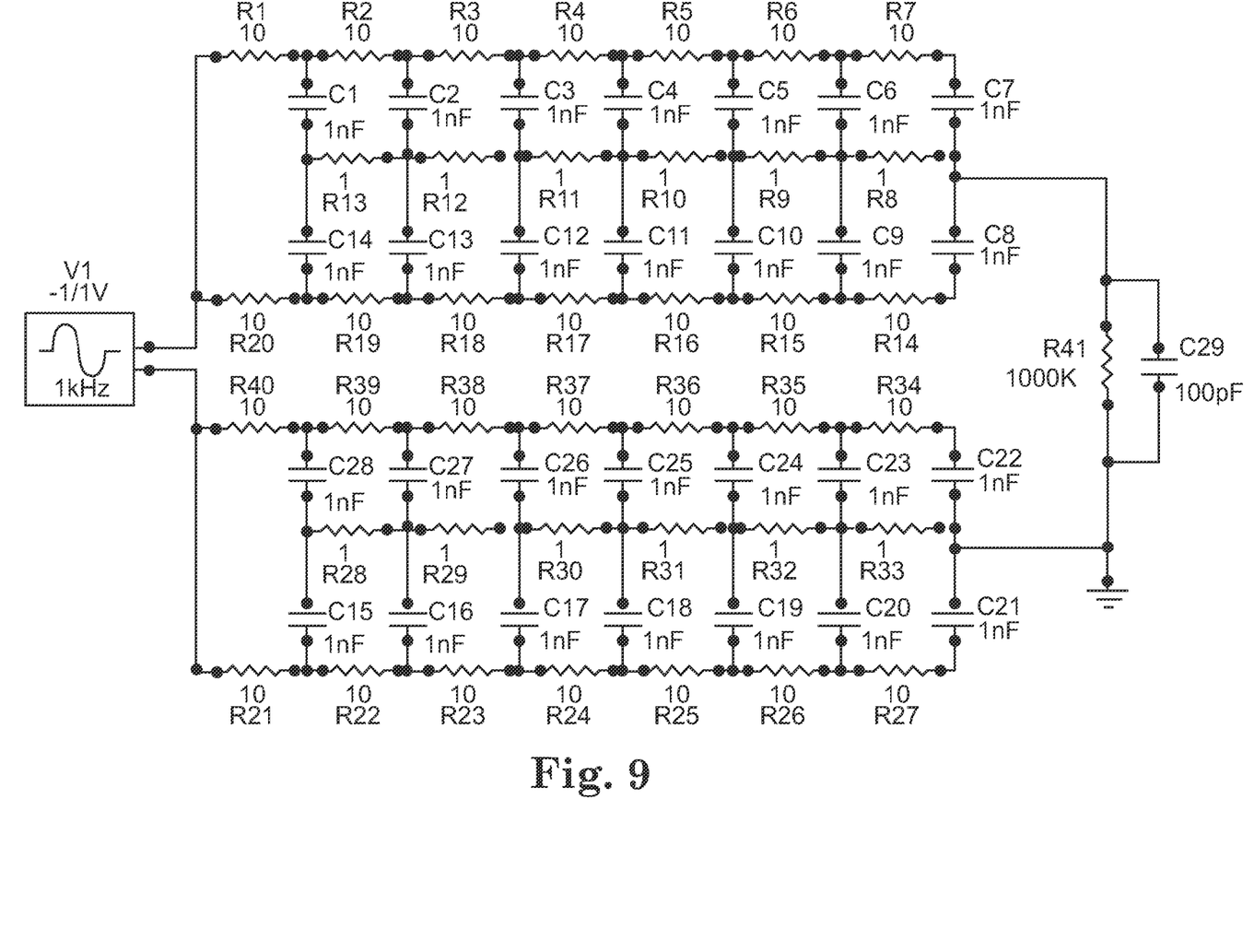
FIG. 9 is a circuit diagram model of a medical electrode in an embodiment according to the present teachings.

With reference to FIG. 9, a circuit diagram model of a medical electrode in an embodiment according to the present teachings is shown. Experimental data verifies the circuit diagram in FIG. 9 as a model for a medical electrode in accordance with the present teachings. Using this circuit diagram allows calculation of the parameters required for a given frequency range. The lower cutoff is determined by the capacitance; the higher the capacitance, the lower the cutoff frequency. Likewise, the resistance of the monitor determines the upper limit, the higher the viewing resister, and the higher the cutoff. With a standard 10M-ohm resister, the frequency is very high. This can be adjusted, however.

Figure 10:
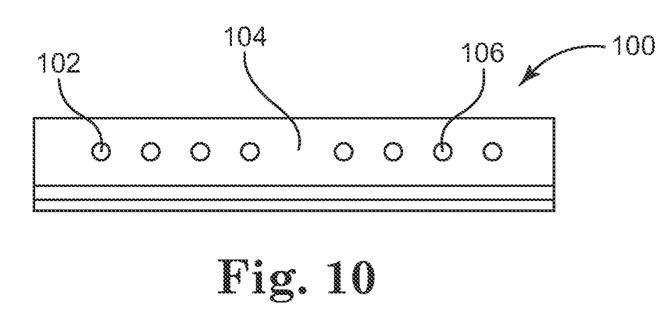
FIG. 10 is a side profile view of a medical electrode in an embodiment according to the present teachings.
Figure 11:
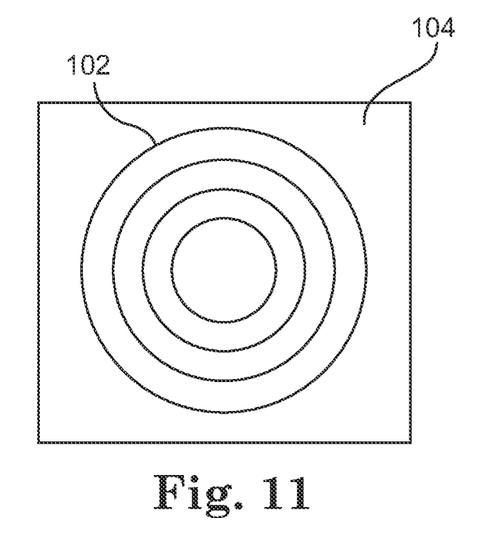
FIG. 11 is a top profile view of a medical electrode in an embodiment according to the present teachings.

With reference to FIGS. 10 and 11, profile views of a medical electrode in embodiments according to the present teachings are shown. The inventors have found that by adding inductance to capacitive electrode 100, fine tuning of electrode 100 can be achieved. A purely capacitive electrode will transmit a square wave as a ramp, with a subsequent decay to baseline similar to a saw tooth waveform. Inductance can balance this tendency and can allow the transmission of a square wave into the tissue essentially unchanged. The added inductance can be achieved by providing concentric rings 102 of ferrous in a layer of gel 104, which is in contact with the skin. Rings 102 are insulated from the electrolyte solution of gel 104 by an inert material 106. Alternatively a number of tiny rings could be randomly imbedded the gel with the rings perpendicular to the flow of current.

Figure 12:
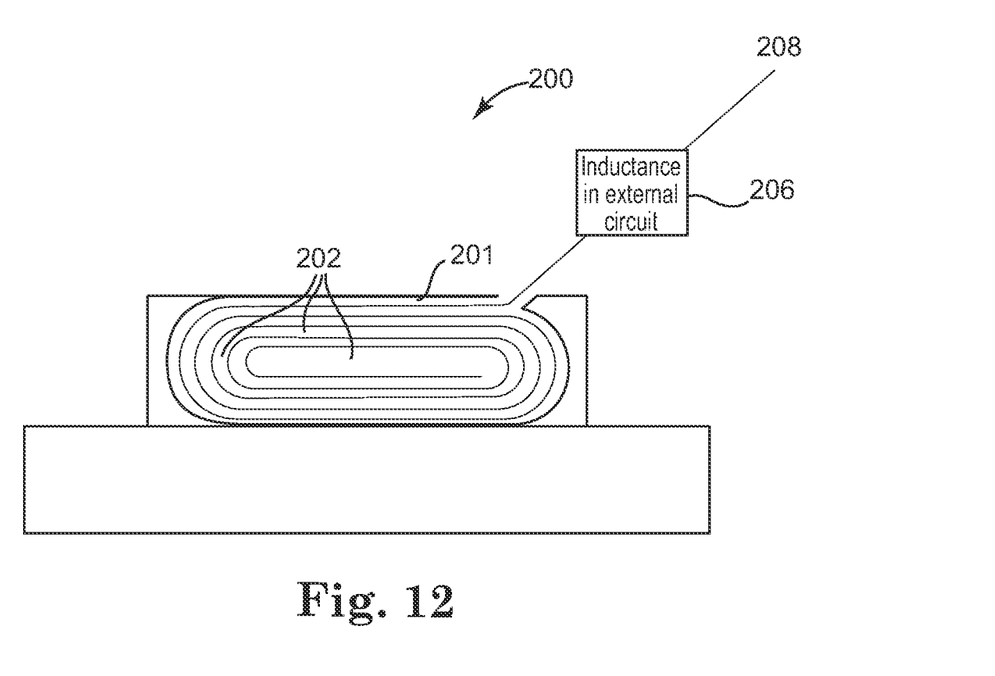
FIG. 12 is a side profile view of a medical electrode in an embodiment according to the present teachings.

With reference to FIG. 12, a side profile of a medical electrode in some embodiments according to the present teachings is shown. By adding tiny spheres 202 of ferric material, which have been coated with insulation, into electrode 200, inductance can affect both the current in the silver ink and the current in gel 204. Alternatively, an inductance circuit 206 can be placed in series with electrode 200 to provide inductance for fine tuning. Circuit 206 could be placed at the tab on electrode 200 or in the circuitry of source 208.

Figure 13:
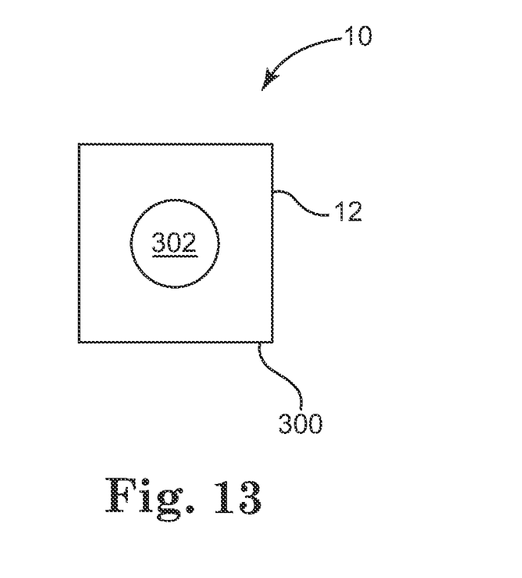
FIG. 13 is a top profile view of a medical electrode in an embodiment according to the present teachings.

With reference to FIG. 13, a top profile view of a medical electrode in an embodiment according to the present teachings is shown. In this embodiment, a layer 300 is added between electrode 10 and the patient that would focus or direct an electric signal. Layer 300 would consist of an insulating sheet with a hole 302. Insulating sheet 300 would have adhesive to attach to the skin. Current would be forced through hole 302. This would allow the signal to be more localized. The current by necessity transverses only the aperture, rather than the entire contact surface as it would without the added layer.

One skilled in the art will appreciate the present teachings can be practiced with embodiments other than those disclosed. The disclosed embodiments are presented for purposes of illustration and not limitation, and the present teachings are limited only by the claims follow.

What is claimed is:

1. A medical electrode for transmitting an electrical signal to a patient, the electrode comprising:
    a conductive ink layer having a top surface and a bottom surface;
    a first dielectric film having an inner facing surface and an outer facing surface, with the inner facing surface operatively connected to the top surface of the conductive ink layer; and
    a layer of conductive substance located on the outer facing surface of the first dielectric film; and
    a second dielectric film having an inner facing surface and an outer facing surface, with the inner facing surface operatively connected to the bottom surface of the conductive ink layer and to the inner facing surface of the first dielectric film;
    wherein the layer of conductive substance is galvanically isolated from the conductive ink layer;
    wherein the conductive ink layer and the layer of conductive substance form a capacitance; and
    wherein the first dielectric film has a thickness that is greater than the conductive ink layer.

2. The electrode of claim 1, wherein the conductive ink layer has a thickness of approximately 0.3 mil (0.007 mm).

3. The electrode of claim 1, wherein the first dielectric film has a thickness of approximately 0.5 mil (0.012 mm).

4. The electrode of claim 1, wherein the second dielectric film has a thickness of approximately 0.5 mil (0.012 mm).

5. The electrode of claim 1, wherein the conductive ink layer, the first dielectric film and the second dielectric film have a combined thickness of approximately 1.3 mil (0.033 mm).

6. The electrode of claim 1, wherein the first and second dielectric films are adhesively attached to each other.

7. The electrode of claim 6, wherein the layer of conductive substance comprises adhesive gel.

8. The electrode of claim 1, wherein the conductive ink comprises metallic material.

9. A medical electrode suitable for capacitive coupling to a patient, the medical electrode comprising:
- a dielectric layer having a first side and a second side;
- conductive ink carried by the first side of the dielectric layer, with the conductive ink comprising a plurality of similarly shaped, sequentially arranged sections; and
- a conductive gel connected to and carried by the second side of the dielectric layer opposite said plurality of sections of conductive ink;
- in which capacitances formed between each section of the conductive ink and conductive gel coating combine to form a total capacitance of the electrode; and
- wherein the total capacitance is greater than 7 nanofarads.

10. The electrode of claim 9, wherein the conductive ink comprises metallic material.

11. The electrode of claim 9, wherein each section has a length of approximately 1.5 inches.

12. The electrode of claim 9, wherein each section has an area of approximately 2 square inches.

13. The electrode of claim 9, wherein at least one section has a capacitance of approximately 7 nanofarads.

14. The electrode of claim 9, wherein the total capacitance has a range of between approximately 7 nanofarads to approximately 40 nanofarads.

15. A capacitive medical electrode suitable for capacitive coupling to a patient, the electrode comprising: a dielectric substrate with first and second opposing surfaces, with the first surface bearing conductive ink and with the second surface bearing an electrolytic gel, with the dielectric substrate being of sufficient size and thickness such that: there is substantially no electrical contact between the conductive ink and the electrolytic gel; the conductive ink and the electrolytic gel form a capacitor; and the dielectric substrate and the conductive ink have a combined thickness of approximately 0.8 mil (0.020 mm).

16. A medical electrode for transmitting an electrical signal to a patient, the electrode consisting essentially of:
- a conductive ink layer having a top surface and a bottom surface;
- a first dielectric film having an inner facing surface and an outer facing surface, with the inner facing surface operatively connected to the top surface of the conductive ink layer; and
- a layer of conductive substance located on the outer facing surface of the first dielectric film;
- wherein the layer of conductive substance is galvanically isolated from the conductive ink layer; and
- wherein the conductive ink layer and the layer of conductive substance form a capacitance.

17. The electrode of claim 16, further consisting essentially of a second dielectric film having an inner facing surface and an outer facing surface, with the inner facing surface operatively connected to the bottom surface of the conductive ink layer and to the inner facing surface of the first dielectric film.

18. A medical electrode for transmitting an electrical signal to a patient, the electrode comprising:
- a conductive ink layer having a top surface and a bottom surface wherein the conductive ink layer includes a non-conductive hole;
- a first dielectric film having an inner facing surface and an outer facing surface, with the inner facing surface operatively connected to the top surface of the conductive ink layer; and
- a layer of conductive substance located on the outer facing surface of the first dielectric film;
- wherein the layer of conductive substance is galvanically isolated from the conductive ink layer;
- wherein the conductive ink layer and the layer of conductive substance form a capacitance; and
- wherein the first dielectric film has a thickness that is greater than the conductive ink layer.

19. The electrode of claim 18, wherein the first dielectric film further comprises a hole, wherein the hole of the first dielectric film is in alignment with the non-conductive hole of the conductive ink layer and wherein the hole of the first dielectric film is smaller than the non-conductive hole of the ink layer.

* * * * *